US00PP18537P2

(12) United States Plant Patent
Zaiger et al.

(10) Patent No.: US PP18,537 P2
(45) Date of Patent: Mar. 4, 2008

(54) **INTERSPECIFIC *PRUNUS* PLANT NAMED 'ESCORT'**

(50) Latin Name: ***Prunus* species**
Varietal Denomination: Escort

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 21 days.

(21) Appl. No.: 11/598,278

(22) Filed: Nov. 13, 2006

(51) Int. Cl.
*A01H 5/00* (2006.01)

(52) U.S. Cl. ..... Plt./180
(58) Field of Classification Search ..... Plt./180
See application file for complete search history.

(56) References Cited

U.S. PATENT DOCUMENTS

PP6,763 P * 4/1989 Zaiger et al. ..... Plt./180

* cited by examiner

*Primary Examiner*—Wendy Haas

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Heavy and regular production of large size fruit.
2. Fruit with an attractive orange flesh and skin color.
3. Vigorous, semi-spreading tree growth.
4. Relatively uniform ripening of fruit throughout the tree.
5. Fruit with a good balance between acid and sugar.
6. Fruit with good handling and shipping quality.

1 Drawing Sheet

Botanical classification: *Prunus* species.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of plum, apricot and interspecific trees, which are known to us, and mentioned herein, 'Coulamar' Apricot (non-patented), 'Patterson' Apricot (U.S. Plant Pat. No. 2,877), 'Mariposa' Plum (U.S. Plant Pat. No. 111), 'Flavor Supreme' Interspecific (U.S. Plant Pat. No. 6,763) and 'Red Beaut' Plum (U.S. Plant Pat. No. 2,539).

ORIGIN OF THE VARIETY

A new and distinct variety of interspecific tree, [*Prunus armeniaca*×(*Prunus armeniaca*×*Prunus persica*)]×[*Prunus salicina*×(*Prunus salicina*×*Prunus armeniaca*)] was developed by us in our experimental orchard located near Modesto, Calif. as a first generation cross between our two proprietary lines of interspecific trees with field identification numbers '352LC164' and '31Z635'. The maternal parent (352LC164) originated as a second generation seedling from crosses of the following, 'Coulamar' Apricot (non-patented), 'Patterson' Apricot (U.S. Plant Pat. No. 2,877) and a proprietary peachcot with field identification number '10W100'. The proprietary peachcot (10W100) originated from an open pollinated seedling apricot tree (parentage unknown). The paternal parent (31Z635) originated as a first generation seedling from crosses of the following parents, proprietary interspecific '7HC250', 'Flavor Supreme' Interspecific (U.S. Plant Pat. No. 6,763) and the proprietary plumcot '4G1180'. The proprietary parent '7HC250' originated as a selected seedling from crosses of the following parents, 'Mariposa' Plum (U.S. Plant Pat. No. 111), 'Red Beaut' Plum (U.S. Plant Pat. No. 2,539) and the proprietary plumcots '4G1180' and '42GA580'. A large number of these first generation crosses were budded on older trees of 'Nemaguard' Rootstock (non-patented) to accelerate earlier fruit production for evaluation. Under close and careful observation, one such seedling, exhibited desirable fruit characteristics and was selected in 2003 for additional asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

A new interspecific tree [(Apricot×Peachcot)×(Plum×Plumcot)] is large, vigorous, semi-spreading in growth and a productive and regular bearer of large, freestone fruit with good flavor and eating quality. The fruit is further characterized by having an attractive orange skin color, firm flesh, holding firm on the tree 12 to 14 days after maturity (shipping ripe) and being relatively uniform in size and maturity throughout the tree. The fruit having good handling, storage and shipping quality, with an average Brix of 16.0°. The tree having a winter chilling requirement of approximately 750 hours at or below 45° F. In comparison to its proprietary interspecific maternal parent '352LC164' the new variety has an attractive orange skin and flesh color, compared to yellow, is higher in soluble solids (Brix) and is approximately 10 days earlier in maturity. In comparison to its proprietary interspecific pollen parent '31Z635', the fruit of the new variety has an attractive orange flesh and pubescent skin, compared to yellow flesh and a smooth slick red skin and is approximately 30 days earlier in maturity.

PHOTOGRAPH OF THE VARIETY

The accompanying color photographic illustration shows typical specimens of the foliage and fruit of the present new interspecific variety. The illustration shows typical specimens of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, 5 years of age, its flowers, foliage and fruit, as based on observations of 5 year old specimens grown near Modesto, Calif., with color in accordance with Munsell Book of Color.

Tree:

Size. —Large. Pruned to 3 to 3.5 meters in height for economical harvesting of fruit. Average spread 3 meters, varies with different cultural practices.

*Vigor.*—Vigorous, tree growth of 1.5 to 2 meters in height the first growing season, varies with type of soil, fertility and cultural practices.

*Form.*—Semi-spreading, crotch angle approximately 40°, increases with heavy crop load.

*Branching habit.*—Semi-spreading, usually pruned to vase shape to allow more sunlight and air movement to center of tree to enhance fruit color and health of fruit spurs.

*Productivity.*—Productive, normal thinning and spacing desired for market size fruit. Set varies with climatic conditions at bloom time.

*Bearer.*—Regular, adequate fruit set 3 consecutive years. No alternate bearing observed.

*Fertility.*—Self fertile, flowers set fruit when isolated under bags.

*Density.*—Medium dense, controlled by pruning.

*Hardiness.*—Tree grown in USDA Hardiness Zone 9. Hardy in all stone fruit growing areas of California. Winter chilling requirement approximately 750 hours at or below 45° F.

Trunk:

*Size.*—Medium. Average circumference 35.5 cm at 30.4 cm above ground on a 5 year old tree.

*Stocky.*—Medium stocky, increases with age of tree.

*Texture.*—Medium shaggy, roughness increases with age.

*Color.*—Varies from 2.5Y 3/4 to 5Y 6/2.

Branches:

*Size.*—Medium stocky. Average circumference 13.7 cm at 0.9 meter above ground. Crotch angle approximately 40°, increases with heavy crop load.

*Surface texture.*—New growth relatively smooth, old growth medium rough, roughness increases with age of tree.

*Lenticels.*—Average number 13 in a 25.8 sq cm section. Size — medium. Average length 3.0 mm. Average width 1.1 mm. Color varies from 10YR 8/8 to 2.5Y 8/8.

*Color.*—New growth varies from 2.5YR 3/6 to 2.5YR 4/4. Old growth varies from 5YR 3/4 to 5YR 4/2, varies with age of growth.

Leaves:

*Size.*—Medium. Average length 72.1 mm. Average width 60.8 mm.

*Form.*—Ovate.

*Apex.*—Cuspidate.

*Base.*—Obtuse.

*Margin.*—Doubly serrate.

*Thickness.*—Medium.

*Surface texture.*—Upper surface, relatively smooth, slightly indented over midrib and leaf veins, glabrous. Lower surface relatively smooth, small ridges created by midrib and pinnate venation, glabrous.

*Petiole.*—Size — medium to large. Average length 34.3 mm. Average width 1.4 mm. Color varies from 5R 3/8 to 10Y 6/6. Varies with amount of exposure to direct sunlight. Very shallow, longitudinal groove, glabrous.

*Glands.*—Type — globose. Size — small. Average length 0.5 mm. Average diameter 0.4 mm. Number — average 2, varies from 1 to 4. Located on upper portion of petiole and lower portion of leaf blade. Color varies from 5R 3/8 to 5GY 5/6.

*Color.*—Upper surface varies from 5GY 4/6 to 5GY 3/6. Lower surface varies from 5GY 4/4 to 5GY 5/4. Midvein color varies from 5GY 8/4 to 5GY 8/6.

Flower buds:

*Size.*—Large. Average length 15.8 mm. Average diameter 12.4 mm.

*Hardiness.*—Hardy in all stone fruit growing areas of California.

*Form.*—Conical, becoming elongated before opening.

*Pedicel.*—Short. Average length 2.7 mm. Average width 2.1 mm. Color varies from 2.5GY 7/4 to 5GY 7/6.

*Color.*—Varies from 7.5RP 8/6 to 10RP 8/4.

*Number of buds per spur.*—Average 5, varies from 4 to 8.

Flowers:

*Size.*—Medium to large. Average height 16.7 mm. Average diameter 23.2 mm.

*Petals.*—Number 5, alternately arranged to sepals. Size — medium to large. Average length 14.2 mm. Average width 15.2 mm. Form — orbicular. Margin — sinuate. Both surfaces glabrous. Color varies from 7.5RP 9/2 to 10RP 9/2, fades with age of flower.

*Sepals.*—Number 5, alternately arranged to petals. Shape — ovate. Margin — entire. Size — large. Average length 7.7 mm. Average width 7.2 mm.

Color — upper surface varies from 7.5RP 4/8 to 7.5RP 3/8. Lower surface varies from 10RP 3/6 to 10RP 3/8. Both surfaces glabrous.

*Stamens.*—Average number per flower — 30. Filament length 11.6 mm. Filament color N 9.5/ (white). Anther color varies from 5Y 8/10 to 5Y 7/8.

*Pollen.*—Abundant, self fertile. Color varies from 2.5Y 7/10 to 5Y 7/12.

*Pistil.*—Usually one. Surface — pubescent. Average length 13.6 mm. Position of stigma approximately same height as anthers. Color varies from 10Y 8/6 to 10Y 7/6.

*Fragrance.*—Slight aroma.

*Blooming period.*—Date of First Bloom Feb. 25, 2005. Date of Petal Fall Mar. 4, 2005, varies with climatic conditions.

*Color.*—Varies from 7.5RP 9/2 to 10RP 9/2. Color fades with age of flower.

*Number flowers per flower bud.*—Usually one, varies from one to three.

*Pedicel.*—Average length 2.8 mm. Average width 2.1 mm. Color varies from 2.5GY 7/6 to 2.5GY 6/6.

Fruit:

*Maturity when described.*—Firm ripe.

*Date of first picking.*—Jun. 2, 2005.

*Date of last picking.*—Jun. 7, 2005, varies slightly with climatic conditions.

*Size.*—Large. Average diameter axially 62.7 mm. Average transversely in suture plane 60.5 mm. Average across suture plane 53.0 mm. Average weight 113.0 grams, varies slightly with fertility of the soil, amount of thinning and climatic conditions.

*Form.*—Nearly globose, slightly elongated and compressed in suture plane.

*Suture.*—Shallow, distinct, extends from base to apex.

*Ventral surface.*—Lipped, well sealed.

*Apex.*—Slightly retuse.

*Base.*—Retuse.

*Cavity.*—Nearly rounded to slightly elongated in suture plane. Average depth 3.4 mm. Average diameter 7.1 mm.

Stem:

*Size.*—Medium. Average length 10.0 mm. Average diameter 3.3 mm.

*Color.*—Varies from 5GY 5/6 to 5GY 6/6.

Flesh:

*Ripens.*—Evenly.

*Texture.*—Firm.

*Fibers.*—Few, small, tender.

*Firmness.*—Firm, considerably firmer than most commercial shipping varieties of apricots.

*Aroma.*—Moderate.

*Amydgalin.*—Undetected.

*Eating quality.*—Good.

*Flavor.*—Good, with a good balance between sugar and acid.

*Juice.*—Moderate, enhances flavor.

*Brix.*—Average 16.0°, varies slightly with amount of fruit per tree and climatic conditions.

*Color.*—Varies from 7.5YR 7/10 to 7.5YR 7/14. Pit cavity varies from 7.5YR 7/14 to 7.5YR 6/14.

Skin:

*Thickness.*—Medium.

*Surface.*—Relatively smooth, very slightly waffled.

*Down.*—Moderate pubescence, very short in length.

*Tendency to crack.*—None.

*Color.*—Varies from 7.5YR 6/14 to 5YR 6/14, darker where exposed to direct sunlight.

*Tenacity.*—Tenacious to flesh.

*Astringency.*—Undetected.

Stone:

*Type.*—Freestone.

*Size.*—Large. Average length 31.9 mm. Average width 24.3 mm. Average thickness 14.1 mm.

*Form.*—Ovoid.

*Base.*—Usually straight, varies from straight to rounded.

*Apex.*—Usually rounded, varies from rounded to slight point. Average length 0.3 mm.

*Surface.*—Slightly pitted throughout, pits vary from round to slightly elongated. A small, narrow groove on each side of suture extending from base to apex.

*Sides.*—Varies from equal to unequal with one side extending further from suture plane.

*Ridges.*—One narrow, small ridge on each side of suture.

*Tendency to split.*—None.

*Color.*—Varies from 7.5YR 2/4 to 10YR 3/4 when dry.

Kernel:

*Form.*—Ovate.

*Viability.*—Viable, complete embryo development.

*Size.*—Large. Average length 21.2 mm. Average width 14.0 mm. Average depth 8.9 mm.

*Skin.*—Color varies from 7.5YR 7/6 to 7.5YR 5/8 when dry.

Use:

*Dessert.*—Market — local and long distance.

Keeping quality: Good, held firm in cold storage 2 weeks at 38° to 42° F. without internal breakdown of flesh, shriveling or appreciable loss of flavor.

Shipping quality: Good, showed minimal flesh bruising or skin scarring during picking and packing trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

What is claimed is:

1. A new and distinct variety of interspecific tree, substantially as illustrated and described, characterized by its large size, vigorous, semi-spreading growth and being a regular and productive bearer of large, firm, freestone fruit with good flavor and eating quality; the fruit is further characterized by holding firm on the tree 12 to 14 days after maturity (shipping ripe), having an attractive orange flesh and skin color and being relatively uniform in size and maturity throughout the tree.

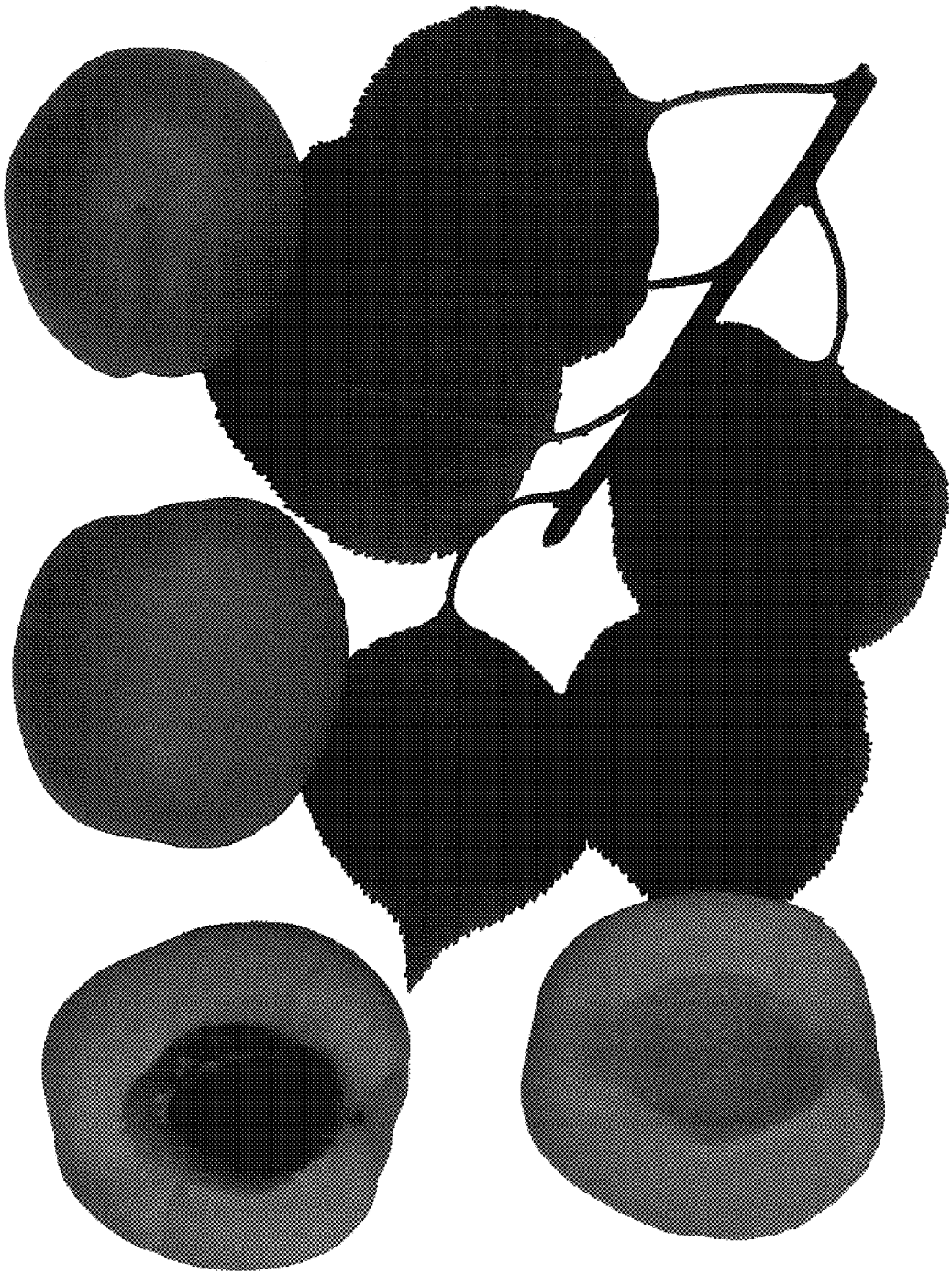

* * * * *